(12) United States Patent
Seneviratne et al.

(10) Patent No.: US 11,369,288 B2
(45) Date of Patent: Jun. 28, 2022

(54) ACTIVITY PULSE

(71) Applicant: NATIONAL ICT AUSTRALIA LIMITED, Eveleigh (AU)

(72) Inventors: Aruna Seneviratne, Eveleigh (AU); Sara Khalifa, Eveleigh (AU); Mahbub Hassan, Eveleigh (AU)

(73) Assignee: NATIONAL ICT AUSTRALIA LIMITED, Eveleigh (AU)

(*) Notice: Subject to any disclaimer, the term of this patent is extended or adjusted under 35 U.S.C. 154(b) by 819 days.

(21) Appl. No.: 16/084,892

(22) PCT Filed: Mar. 14, 2017

(86) PCT No.: PCT/AU2017/050224
§ 371 (c)(1),
(2) Date: Sep. 13, 2018

(87) PCT Pub. No.: WO2017/156576
PCT Pub. Date: Sep. 21, 2017

(65) Prior Publication Data
US 2019/0076062 A1 Mar. 14, 2019

(30) Foreign Application Priority Data
Mar. 14, 2016 (AU) .............................. 2016900938

(51) Int. Cl.
*A61B 5/11* (2006.01)
*H02N 2/18* (2006.01)
(Continued)

(52) U.S. Cl.
CPC .......... *A61B 5/1118* (2013.01); *A61B 5/7264* (2013.01); *G04B 47/06* (2013.01);
(Continued)

(58) Field of Classification Search
CPC ... A61B 5/1118; A61B 5/7264; A61B 5/6895; A61B 2560/0214; G04B 47/06; H02N 2/18; G16H 50/20
(Continued)

(56) References Cited

U.S. PATENT DOCUMENTS

2010/0045119 A1* 2/2010 Jackson ............... H02K 7/1876
310/20
2011/0193350 A1* 8/2011 Rastegar .................. H02N 2/18
290/1 R
(Continued)

FOREIGN PATENT DOCUMENTS

EP 0 816 986 A2 1/1998
EP 0816986 A2 * 1/1998 ........... A61B 5/6831

OTHER PUBLICATIONS

Khalifa, S. et al. (Energy-Harvesting Wearables for Activity-Aware Services', IEEE Internet Computing, IEEE, Aug. 31, 2015, vol. 19, Iss. 5, pp. 8-16).*
(Continued)

*Primary Examiner* — Omar Casillashernandez
(74) *Attorney, Agent, or Firm* — Ladas & Parry LLP

(57) ABSTRACT

Described is device for monitoring an activity. The device comprises a transducer that generates electric power from the activity and an energy store that stores the electric power over consecutive time intervals. The device further comprises a transmitter that periodically transmits the stored energy as an activity pulse indicative of an activity classification.

22 Claims, 5 Drawing Sheets

(51) Int. Cl.
*A61B 5/00* (2006.01)
*G04B 47/06* (2006.01)
(52) U.S. Cl.
CPC .............. *H02N 2/18* (2013.01); *A61B 5/6895* (2013.01); *A61B 2560/0214* (2013.01)
(58) Field of Classification Search
USPC ......................................................... 310/339
See application file for complete search history.

(56) References Cited

U.S. PATENT DOCUMENTS

| | | | | |
|---|---|---|---|---|
| 2013/0158686 | A1* | 6/2013 | Zhang | A61B 5/1123 700/91 |
| 2013/0217979 | A1* | 8/2013 | Blackadar | A61B 5/1123 600/301 |
| 2015/0068069 | A1* | 3/2015 | Tran | A43B 3/34 340/693.1 |
| 2016/0346584 | A1* | 12/2016 | Schneider | H01L 27/16 |
| 2019/0000332 | A1* | 1/2019 | Li | A61B 5/681 |
| 2019/0076062 | A1* | 3/2019 | Seneviratne | A61B 5/1118 |

OTHER PUBLICATIONS

International Search Report (ISR) and Written Opinion (WO) dated Mar. 22, 2017 for Application No. PCT/AU2017/050224.

* cited by examiner

ACTIVITY PULSE

RELATED APPLICATION

This application is an application under 35 U.S.C. 371 of International Application No. PCT/AU2017/050224 filed on Mar. 14, 2017, the entire contents of which are incorporated herein by reference.

TECHNICAL FIELD

This disclosure relates to reducing energy consumption of a sensor system. In one form power consumption is reduced for a sensor system that uses harvested kinetic energy.

BACKGROUND

One of the challenges in sensor systems is meeting the power requirements where the systems are wireless or rely on batteries. One possible solution is to harvest energy from the system environment and to use this harvested energy to provide power to the sensor system. Energy can be harvested from a number of different sources, such as solar power, thermal energy (or temperature gradients), wind energy, electromagnetic energy, salinity gradients and kinetic energy from movement or vibration.

One example of a sensor system suitable for energy harvesting is wearable technology. Wearable technology includes activity-aware services that make use of human activity recognition (HAR) in various domains like healthcare and indoor positioning. Battery life is a problem with wearable HAR technology. Wearables therefore either need large batteries or the batteries must be charged regularly in order to achieve sustained operation. However the amount of energy that can be harvested is generally small in comparison to the power requirements of the HAR application.

Conventional sensor systems typically have (1) a sensing component that provides sensed data, (2) a processor for extracting data from the sensed data, and (3) a component for distributing the sensed and/or processed data (e.g. memory or a transmitter). A power source that provides power for all three of these components of the system is required. If the power source relies (either wholly or in part) on harvested energy for the power supply then it would be beneficial to reduce the power requirements of one or more of the three components.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

One way of reducing the power requirements of a wearable HAR device is to remove the sensing component by incorporating the sensing functionality into a transducer used for energy harvesting. Such a system comprises a transducer that generates an electric signal from ambient energy, and a processor adapted to process the electric signal to determine and output an identifier or characteristic of a source of the ambient energy (such as an activity classification).

However, activity classification using the harvested electric signal would still consume significant power in the device. Even if the classification is done in a server or remote computer, then energy consumption due to communication of large amounts of voltage data to that computer or server would consume significant power.

In one aspect there is provided a device for monitoring an activity, the device comprising: a transducer that generates electric power from the activity; an energy store that stores the electric power over consecutive time intervals; and a transmitter that periodically transmits the stored energy as an activity pulse indicative of an activity classification.

As used herein, "activity pulse" refers to an unmodulated voltage pulse that gets transmitted from an energy store (e.g. a capacitor), where harvested energy is stored over a time interval resulting in an amount of harvested power for the respective time interval. Therefore the activity pulse is a voltage pulse with an amplitude related to the amount of power in the pulse. The amount of power in the pulse is in turn related to the amount of energy that has been harvested and stored over the respective time interval.

The activity classification may be selected from a group consisting of: walking, running, ascending stairs, descending stairs, and standing.

The transducer may be a kinetic energy harvester. The transducer may be a piezoelectric transducer with a cantilevered beam configuration. The transducer may be adapted for operation in a frequency range associated with the activity. The transducer may comprise two or three orthogonal transducers providing multi-axial electric signals that comprise identifying features associated with directions of the activity.

The consecutive time intervals may be fixed length time intervals, each between 1 and 30 seconds in length.

The device may be in communication with a remote computing device configured to receive the transmitted activity pulse and to determine the activity classification from the received activity pulse.

In another aspect there is provided a system for classifying an activity, the system comprising: an activity monitoring device that comprises: a transducer that generates electric power from the activity; an energy store that stores the electric power over consecutive time intervals; and a transmitter that periodically transmits the stored energy as an activity pulse indicative of an activity classification; and a remote computing device in communication with the activity monitoring device, the remote computing device comprising: a receiver for receiving the transmitted activity pulse; and a processor with a memory having instructions for determining the activity classification from the received activity pulse.

The processor may determine the activity classification based on Bayesian decision theory. The processor may determine the activity classification based on the mean power or the power distribution of the received pulse. The processor may, responsive to the activity classification, output a control signal.

In another aspect there is provided a method for monitoring an activity, the method comprising: harvesting kinetic energy from the activity; storing the harvested energy over consecutive time intervals; and transmitting the stored energy as an activity pulse indicative of an activity classification.

The method may further comprise: receiving the transmitted activity pulse; determining the activity classification from the received activity pulse; and outputting the determined activity classification.

The determining may comprise: determining a statistical parameter of the received activity pulse; comparing the determined statistical parameter with a saved parameter; and responsive to the comparing, classifying the activity.

The statistical parameter may be a power distribution over a time interval. The statistical parameter may be a mean power of the received activity pulse over a time interval.

The time interval may be between 1 and 20 seconds.

The determining may be based on Bayesian decision theory.

The method may further comprise determining the saved parameter.

The determined activity classification may be output to a portable device.

As used herein, except where the context requires otherwise, the term "comprise" and variations of the term, such as "comprising", "comprises" and "comprised", are not intended to exclude further additives, components, integers or steps.

BRIEF DESCRIPTION OF DRAWINGS

Embodiments of the disclosure are now described by way of example with reference to the accompanying drawings in which.

DESCRIPTION OF EMBODIMENTS

Conventional systems used for determining characteristics of movement, e.g. to provide activity-aware services such as with wearable HAR systems, typically make use of accelerometers to obtain data about the activities. However, the power requirement of accelerometers is significant, and has been shown to range between 0.35 and 5 times the harvested kinetic energy when detecting common human activities (e.g. walking and running). Some activities generate only a few μW, not enough to power both an accelerometer and radio communication required to transmit the sensed data. The power needs of a wearable device can be reduced by replacing the sensing functionality of an accelerometer with similar functionality provided by an energy harvesting transducer. The harvested signal can provide information about the source from which the energy was harvested from so that a separate sensor is not required. In addition, a further power saving can be achieved by reducing (or even altogether removing) the data processing required to extract information from the signal, at least at the wearable device where power consumption needs to be reduced.

The system described herein can be used for a wearable (or implantable) device that is used for activity monitoring generally, e.g. human activity monitoring.

Figure 1:
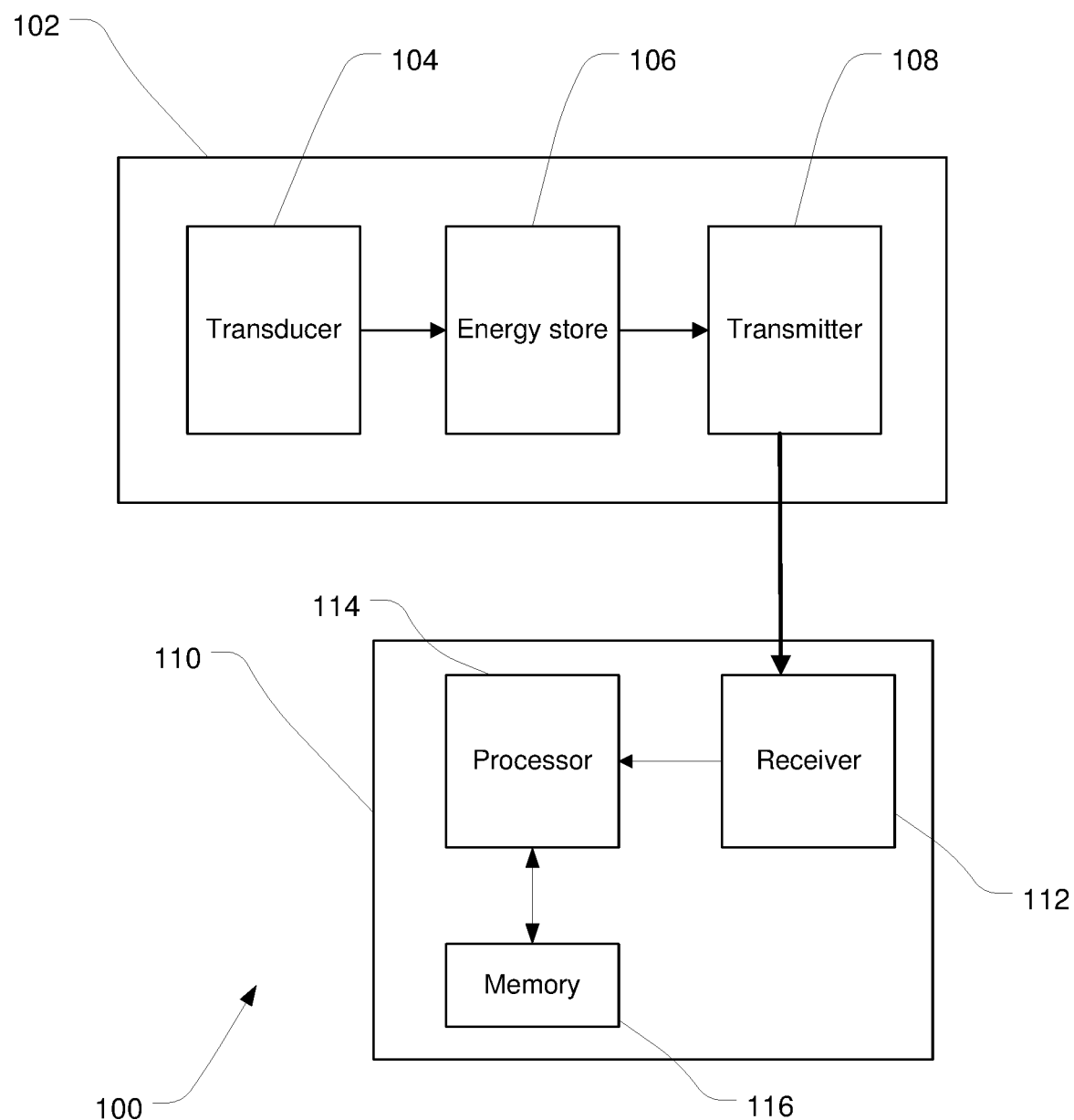
FIG. 1 is a schematic representation of an embodiment of a system for identifying an activity.

FIG. 1 is a schematic representation of a system 100 for classifying an activity that uses kinetic energy harvesting. The system 100 includes a human activity monitor (HAM) 102 that, instead of using an accelerometer to obtain data about the activity, uses a transducer 104 that harvests ambient energy, and the power generated from the harvested energy provides information about the activity. The HAM 102 has an energy store 106, typically in the form of a capacitor, that stores the harvested power over a certain time interval, for example a time window of 1, 5, 10 or 20 seconds etc. A transmitter 108 transmits the stored power in the form of an unmodulated signal (referred to as the activity pulse) at the end of every time window, this transmission effectively emptying the energy store 106 before the next time interval commences. The activity pulse is therefore an unmodulated short burst of voltage, the amplitude of which is indicative of the total power stored over a respective time interval.

The time interval may be a fixed interval. The time interval may also be variable, for example depending on the user's activity.

All the stored energy is used to transmit a short pulse. The pulse duration is short, for example between a few nanoseconds and a few milliseconds, to achieve high transmission power, because the shorter the pulse, the higher the power given the same amount of energy used.

In this embodiment the energy is stored over fixed time intervals so that the total energy transmitted in each activity pulse varies. In other embodiments the energy store 106 is filled, and the maximum energy that can be saved in the energy store 106 is transmitted at varying time intervals depending on how long it takes to fill the energy store 106. The activity at the received is determined by analysing how frequently the pulses are received, while all pulses have the same power.

The system 100 includes a remote computing device 110 that has a receiver 112 for receiving the transmitted activity pulse, a processor 114 for determining the activity from the received activity pulse, and memory 116 associated with the processor 114. The remote computing device 110 may be any suitable device, such as a smart phone, that includes a receiver compatible with the transmission protocol used (e.g. the Bluetooth low energy (BLE) protocol), and includes a processor and memory.

In this embodiment the transducer 104 is a piezoelectric transducer with a cantilevered beam configuration. When the piezoelectric material is subjected to a mechanical stress due to any source of environmental vibrations, it expands on one side and contracts on the other. Positive charges accumulate on the expanded side and negative charges on the contracted side, generating an AC voltage as the beam oscillates around the neutral position. The amount of voltage is proportional to the applied stress, which means that different vibration patterns would generate different AC voltage patterns. An example of a piezoelectric KEH transducer is the MIDE Volture transducer. In some embodiments the transducer is adapted for operation in a frequency range associated with the activity, for example a 1-10 Hz range for human movement such as walking, running and climbing stairs. In some embodiments, the transducer comprises two or three orthogonal transducers providing multi-axial electric signals that comprise identifying features associated with multiple directions of the activity.

Figure 2:
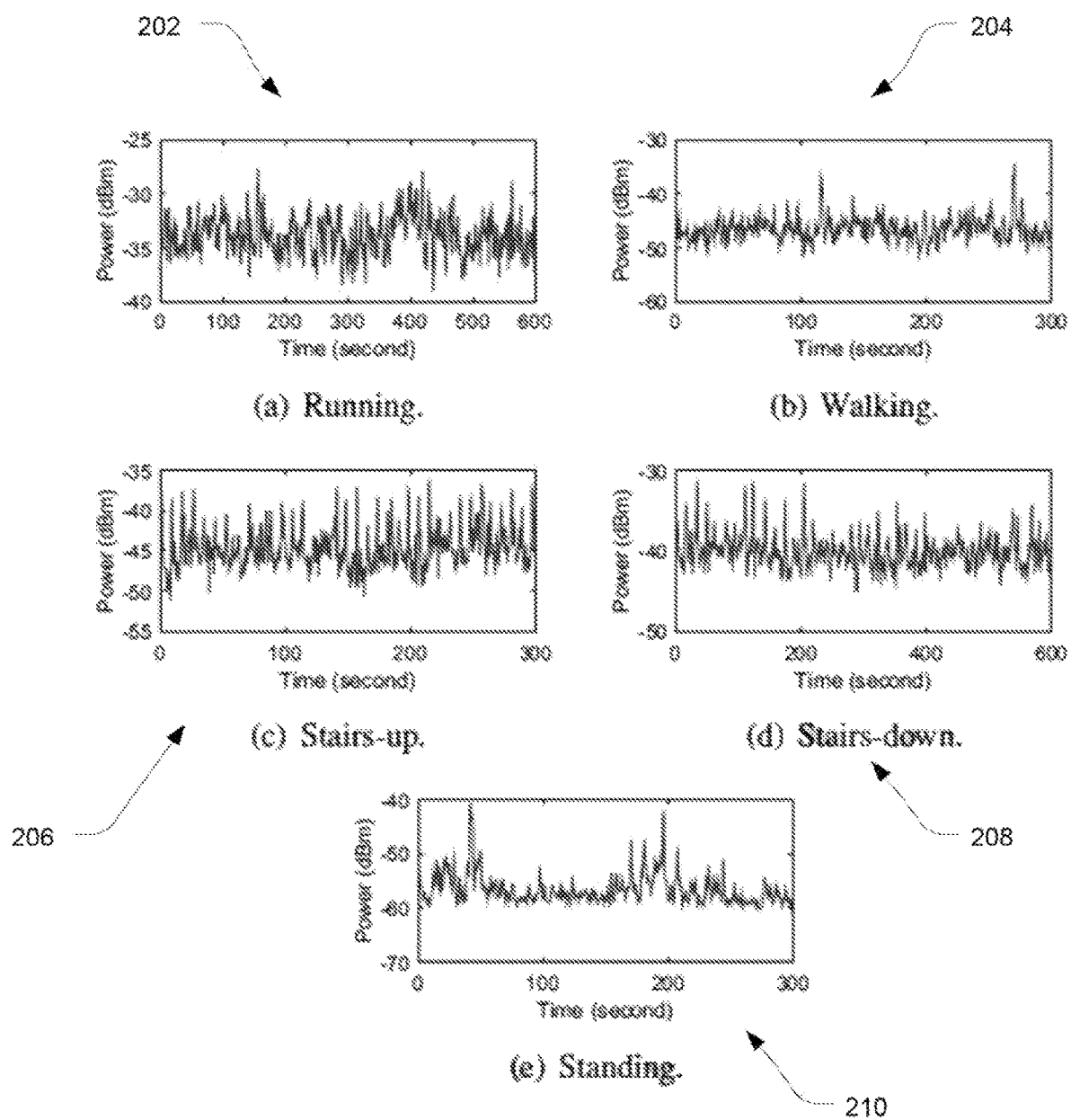
FIG. 2 shows graphs of harvested power for each of five activities.

Because different activities generate power at different rates, the harvested signal strengths over a time interval are different for different activities. Thus, those signal strengths can be used to classify the activities. FIG. 2 shows harvested power signals for running 202, walking 204, ascending stairs 206, descending stairs 208, and standing 210 over a time interval of 300 or 600 seconds. Even these unprocessed power signals are distinctive for the different activities.

Figure 3:
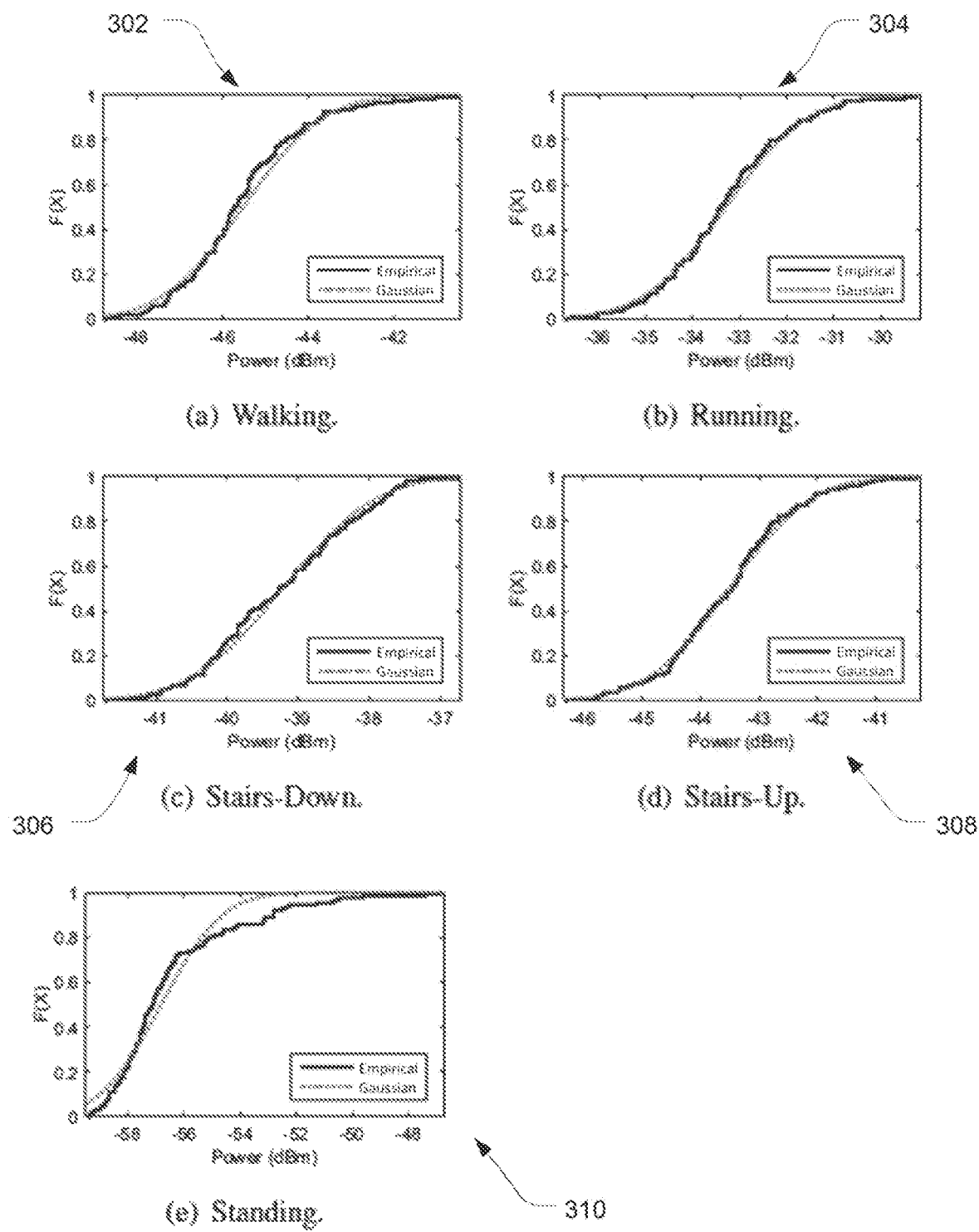
FIG. 3 shows cumulative distribution functions for the power harvested for each of five activities.

FIG. 3 shows the cumulative power distribution functions of the harvested power for walking 302, running 304, descending stairs 306, ascending stairs 308, and standing 310. The harvested power follows Gaussian distributions for each activity. An example of the estimated mean and standard deviations of the Gaussian distributions of power with a time window of w=10 seconds is shown below in Table 1. In this embodiment, the time window is a fixed length time window.

TABLE 1

Estimated mean and standard deviation for the Gaussian distributions of power for different activities.

| Activity | Mean μ [dBm] | Standard deviation σ |
|---|---|---|
| Standing | −56.41 | 2.38 |
| Walking | −45.53 | 1.47 |
| Running | −33.30 | 1.38 |
| Ascending stairs | −43.51 | 1.10 |
| Descending stairs | −39.22 | 1.02 |

The transmitter 108 may be any suitable low energy transmitter, for example supporting the Bluetooth low energy (BLE) protocol. The transmitted signal strength is give by:

$$\text{Power}_{Tx}(i) = \text{Power}_H(i) + 10 \log_{10} K$$

where $\text{Power}_H$ is the harvested power and K is the transmission power amplification factor. The transmitted signal strength is therefore a function of K, which in turn depends on the accumulation time of the harvested energy in the capacitor. The longer the accumulation window, the higher the transmitted signal strength.

Figure 4:
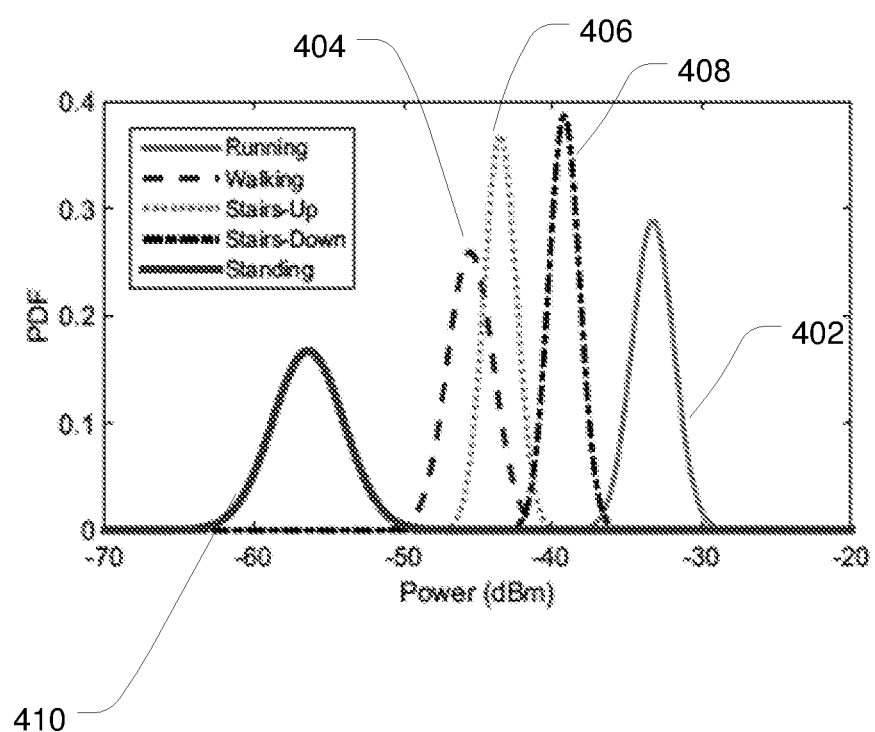
FIG. 4 shows the power distribution function for the transmitted power associated with each of five activities.

As shown in FIG. 4 of the drawings, the transmitted signal strength for each of running 402, walking 404, ascending stairs 406, descending stairs 408, and standing 410 has a distinctive power distribution function (PDF).

Figure 5:
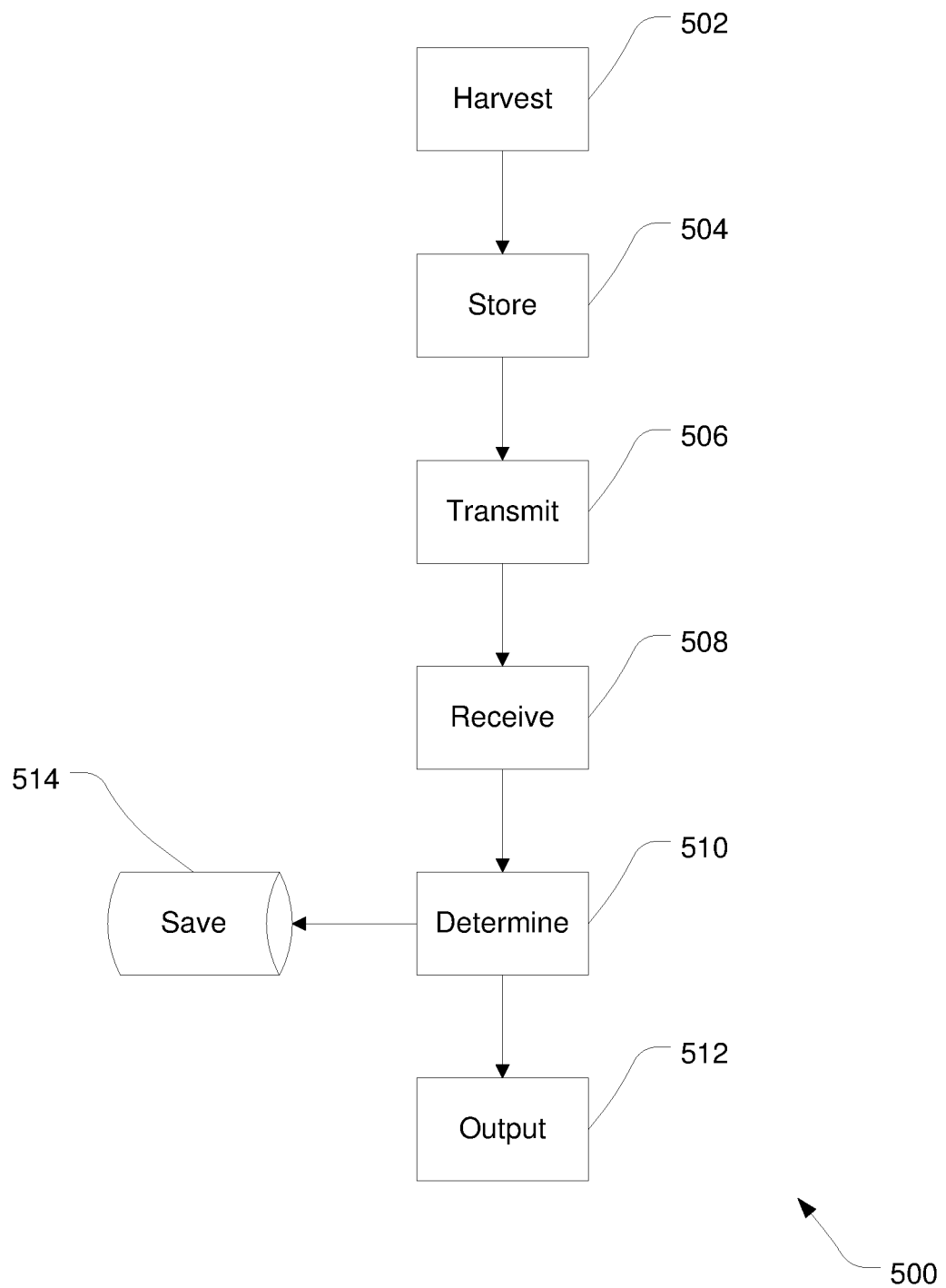
FIG. 5 is a flow diagram of an embodiment of a method for classifying an activity.

With reference to FIG. 5 of the drawings, a flow diagram of an embodiment of a method for identifying an activity is illustrated and is designated generally by the reference numeral 500. At 502 the HAM 102 harvests kinetic energy that is then stored in a capacitor at 504. The stored energy is periodically transmitted at 506 as an activity pulse, and at 508 the activity pulse is received by the remote computing device 110. At 510 the type or classification of the activity is determined from the characteristics of the received activity pulse, and this determined data is saved at 514 and/or output to the user at 512.

Determining the activity classification at 510 relies on the fact that different activities generate power at different rates, so that the received signal would have different signal strengths depending on the relevant activity or class. To determine the activity classification at 510, in one embodiment the remote computer 110 uses Bayesian decision theory to classify activities based on the detected signal strength of the received pulse. Bayesian decision theory is a statistical approach suitable for decision making and pattern recognition, and it requires the analysis of the distributions of the power signals of the activities.

Using Bayesian decision theory, an observation (in this case a received activity pulse) will be classified as one of the five considered activities based on the likelihood of that observation matching the power distribution of a specific activity classification over the selected time window.

It will be understood that, in order for the computing device 110 to determine 410 the activity classification in this way, the computing device 110 will have stored in its memory representative or exemplary distributions for the various activities. In some embodiments, the method includes determining these exemplary distributions, for example by training the processor of the computing device 110 with training data.

Classification methods other than Bayesian decision theory can be used. For example, statistical and machine learning classification can be applied using parameters of the received activity pulses such as the rate of change in received power over time. The received pulses may also be processed further in either the time domain or the frequency domain by applying Fourier and Wavelet transforms.

The accuracy of the method described herein is a function of the transmitted and received signal strength. As described above with reference to the transmitted signal, the longer the accumulation window, the better the results. However, this comes at the cost of increased latency. The received strength, in turn, is a function of the distance between the transmitter and the receiver. Increasing the distance reduces the received signal strength and as a result reduces the accuracy of the results.

It has been found that, using an accumulation window of around 10 seconds and a distance separating the transmitter and receiver of less than 60 cm, the accuracy with which the activity can be classified is in the order of 85%. This comes with the significant advantage of near energy neutrality for several of the functions performed by a wearable HAM.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A device for monitoring an activity, the device comprising:
a transducer that generates electric power from the activity;
an energy store that stores the electric power over consecutive time intervals as stored energy; and
a transmitter that periodically transmits the stored energy as an activity pulse indicative of an activity classification.

2. The device of claim 1 wherein the activity classification is selected from a group consisting of: walking, running, ascending stairs, descending stairs, and standing.

3. The device of claim 1 wherein the transducer is a kinetic energy harvester.

4. The device of claim 3 wherein the transducer is a piezoelectric transducer with a cantilevered beam configuration.

5. The device of claim 3 wherein the transducer is adapted for operation in a frequency range associated with the activity.

6. The device of claim 1 wherein the transducer comprises two or three orthogonal transducers providing multi-axial electric signals that comprise identifying features associated with directions of the activity.

7. The device of claim 1 wherein the consecutive time intervals are fixed length time intervals, each between 1 and 30 seconds in length.

8. The device of claim 1 wherein the device is in communication with a remote computing device configured to receive the activity pulse and to determine the activity classification from the activity pulse.

9. The device of claim 1, wherein the activity pulse is an unmodulated short burst of voltage with an amplitude that is indicative of a total power stored over a respective time interval.

10. A system for classifying an activity, the system comprising:
an activity monitoring device that comprises:
a transducer that generates electric power from the activity;
an energy store that stores the electric power over consecutive time intervals as stored energy; and
a transmitter that periodically transmits the stored energy as an activity pulse indicative of an activity classification; and
a remote computing device in communication with the activity monitoring device, the remote computing device comprising:
a receiver for receiving the activity pulse; and
a processor with a memory having instructions for determining the activity classification from the activity pulse.

11. The system of claim 10 wherein the processor determines the activity classification based on Bayesian decision theory.

12. The system of claim 10 wherein the processor determines the activity classification based on the mean power or the power distribution of the activity pulse.

13. The system of claim 10 wherein the processor, responsive to the activity classification, outputs a control signal.

14. A method for monitoring an activity, the method comprising:
harvesting kinetic energy from the activity;
storing the harvested energy over consecutive time intervals as stored harvested energy; and
transmitting the stored harvested energy as an activity pulse indicative of an activity classification.

15. The method of claim 14 further comprising:
receiving the activity pulse;
determining the activity classification from the activity pulse; and
outputting the determined activity classification.

16. The method of claim 15 wherein the determining comprises:
determining a statistical parameter of the activity pulse;
comparing the determined statistical parameter with a saved parameter; and
responsive to the comparing, classifying the activity.

17. The method of claim 16 wherein the statistical parameter is a power distribution over a time interval.

18. The method of claim 16 wherein the statistical parameter is a mean power of the activity pulse over a time interval.

19. The method of claim 17 wherein the time interval is between 1 and 20 seconds.

20. The method of claim 15 wherein the determining is based on Bayesian decision theory.

21. The method of claim 16 wherein the method further comprises determining the saved parameter.

22. The method of claim 15 wherein the determined activity classification is output to a portable device.

* * * * *